United States Patent
Schlorff et al.

(10) Patent No.: US 7,582,050 B2
(45) Date of Patent: Sep. 1, 2009

(54) APPARATUS FOR HYPERTHERMIA AND BRACHYTHERAPY DELIVERY

(75) Inventors: Jaime L. Schlorff, Phoenixville, PA (US); Paul R. Stauffer, San Rafael, CA (US)

(73) Assignees: The Regents of the University of California, Oakland, CA (US); Bionix Development Corporation, Toledo, OH (US)

( * ) Notice: Subject to any disclaimer, the term of this patent is extended or adjusted under 35 U.S.C. 154(b) by 514 days.

(21) Appl. No.: 11/093,717

(22) Filed: Mar. 30, 2005

(65) Prior Publication Data

US 2005/0251235 A1 Nov. 10, 2005

Related U.S. Application Data

(60) Provisional application No. 60/558,162, filed on Mar. 31, 2004.

(51) Int. Cl.
*A61N 5/02* (2006.01)
(52) U.S. Cl. ......................................................... 600/2
(58) Field of Classification Search .................. 600/2, 600/1–8; 607/101, 154, 156
See application file for complete search history.

(56) References Cited

U.S. PATENT DOCUMENTS

| | | | |
|---|---|---|---|
| 4,556,070 A * | 12/1985 | Vaguine et al. ............. 607/156 |
| 4,947,842 A | 8/1990 | Marchusky et al. |
| 5,334,193 A * | 8/1994 | Nardella ....................... 606/41 |
| 5,429,582 A | 7/1995 | Williams |
| 5,931,774 A * | 8/1999 | Williams et al. ............... 600/2 |
| 6,022,308 A | 2/2000 | Williams |
| 6,083,148 A | 7/2000 | Williams |
| 6,330,479 B1 | 12/2001 | Stauffer |
| 6,349,412 B1 * | 2/2002 | Dean .............................. 2/102 |
| 6,428,504 B1 * | 8/2002 | Riaziat et al. .................. 604/65 |
| 2002/0072645 A1 | 6/2002 | Chornenky et al. |
| 2003/0069619 A1 * | 4/2003 | Fenn et al. ................... 607/101 |
| 2004/0109823 A1 * | 6/2004 | Kaplan ....................... 424/1.11 |

* cited by examiner

*Primary Examiner*—Charles A Marmor, II
*Assistant Examiner*—Christine D Hopkins
(74) *Attorney, Agent, or Firm*—Marshall & Melhorn LLC

(57) ABSTRACT

A combination applicator is able to deliver heat and radiation, either simultaneously or sequentially, for the treatment of cancer or other disease. The combination applicator is flexible and able to conform to contoured anatomy of the patient. The combination applicator comprises a flexible, dielectric containing compartment having a tissue-engaging surface and an opposite, non-tissue-engaging surface. A heating surface comprising one or more RF or microwave antennas or ultrasound transducers is supported adjacent to the non-tissue-engaging surface. In addition, a plurality of conduits are also supported on the dielectric containing compartment, the conduits being adapted to communicate with at least one brachytherapy source. Additional conduits may be located on the tissue contacting surface of the dielectric containing compartment to accommodate moving or stationary temperature monitoring sensors.

24 Claims, 4 Drawing Sheets

APPARATUS FOR HYPERTHERMIA AND BRACHYTHERAPY DELIVERY

RELATED APPLICATION

This application is claiming the benefit, under 35 U.S.C. § 119(e), of the provisional application filed Mar. 31, 2004 under 35 U.S.C. § 111(b), which was granted Ser. No. 60/558,162. This provisional application is hereby incorporated by reference.

BACKGROUND OF THE INVENTION

The invention relates to an apparatus that can deliver heat and radiation either simultaneously or sequentially for the treatment of cancer or other disease.

Hyperthermia therapy consists of heating tissue to a temperature above 41 degrees Celsius. It is well known that in addition to destroying cancer cells, hyperthermia can enhance the therapeutic effects of other treatments, such as radiation, chemotherapy, biological therapies and surgery.

Studies have shown that the therapeutic effect is enhanced when hyperthermia and radiation are delivered simultaneously or within a very short time interval. Certain devices are known that can combine heat with other treatments in a single applicator system. For instance, U.S. Pat. No. 4,947,842 describes a method and apparatus for treating tissue interstitially with multiple modalities of treatment. Designed to be inserted into a tumor, this apparatus comprises a semi-rigid elongated member that is implanted into the malignant tumor. The elongated member contains a hollow passageway that can be configured to deliver heat, radiation or a sequence of both to the surrounding disease. The elongated member can be coated with an anti-cancer drug or other treatment.

U.S. Pat. Nos. 6,083,148, 5,429,582 and 6,022,308 all describe implantable devices for treating brain tumors. These devices can be configured to deliver heat therapy and/or radiation therapy and/or chemotherapy to surrounding tissue.

Published US patent application US2002/72645 A1 describes a device for simultaneously treating a tumor or cancerous growth with both hyperthermia and X-ray radiation using brachytherapy sources inserted into the tumor via needle-like introducers that also serve as microwave antennas. Microwaves are emitted from the introducer to increase the temperature of surrounding cancerous body tissue while a cooling system is included to control the temperature of the introducer surface. The implanted device heats and delivers radiation to the tissue from the inside out. Temperature sensors implanted around the periphery of the tumor monitor the temperature of the treated tissue.

U.S. Pat. No. 6,330,479 describes a microwave antenna array applicator for uniformly heating large areas of contoured anatomy for treatment of skin and superficial tissue disease such as chestwall recurrence of breast carcinoma, or for the diagnosis or treatment of other skin conditions that can benefit from tissue reoxygenation or increased blood perfusion and blood vessel permeability. The microwave applicator includes a flexible, dielectric-containing compartment (containing, e.g., temperature regulated water or oil) having a variable contour, tissue-engaging surface and an opposite non-tissue-engaging surface with an antenna array adjacent to the non-tissue-engaging surface.

Existing hyperthermia treatment methods are not designed to allow delivery of heat and radiation treatments simultaneously in the case of superficial disease near the surface of the body. Therefore, a new device is required that can deliver controlled heat either simultaneously or very close in time to radiation treatments for superficial disease.

SUMMARY OF THE INVENTION

The present invention is directed to a combination applicator that is able to deliver heat and radiation either simultaneously or sequentially for the treatment of cancer or other disease. The combination applicator is flexible and able to conform to the contoured anatomy of the patient. The combination applicator comprises a dielectric containing compartment having a tissue-engaging surface and an opposite, non-tissue-engaging surface. A heating array is supported adjacent to the non-tissue-engaging surface. In addition, a plurality of conduits are also supported on the device, the conduits being adapted to communicate with at least one brachytherapy source.

BRIEF DESCRIPTION OF THE DRAWINGS

The above, as well as other advantages of the present invention, will become readily apparent to those skilled in the art from the following detailed description when considered in light of the accompanying drawings in which.

DETAILED DESCRIPTION OF THE INVENTION

Figure 1:
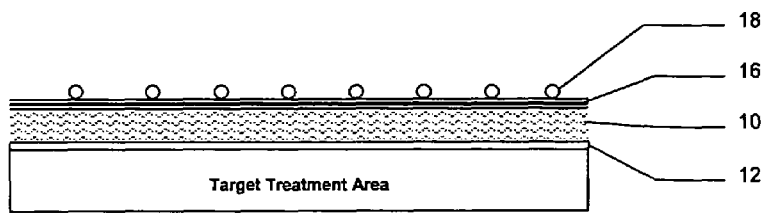
FIG. 1 is a cross-sectional view of a basic combination applicator in accordance with the invention.

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

This invention relates to an applicator for delivering heat and radiation from a single device to treat areas of superficial disease (i.e. tissue<5 cm from the tissue surface). It should be understood that the invention can be applied to treat internal organs of the body that are accessed through standard intraoperative surgical procedures.

Referring to the drawings, the applicator includes a dielectric containing compartment 10, a heating array 16 for the delivery of heat, and provision for the delivery of ionizing radiation. The dielectric containing compartment 10 is a flexible, surface conforming layer of controlled thickness containing a temperature-regulated dielectric material (e.g. distilled water, silicone oil) for coupling heat and radiation into the tissue surface. This compartment is placed in contact with the tissue surface. The compartment is formed of a flexible material that will retain the dielectric therewithin, and is preferably formed of a flexible polymeric or elastomeric material, such as polyvinyl chloride (PVC) or polyurethane.

Figure 2:
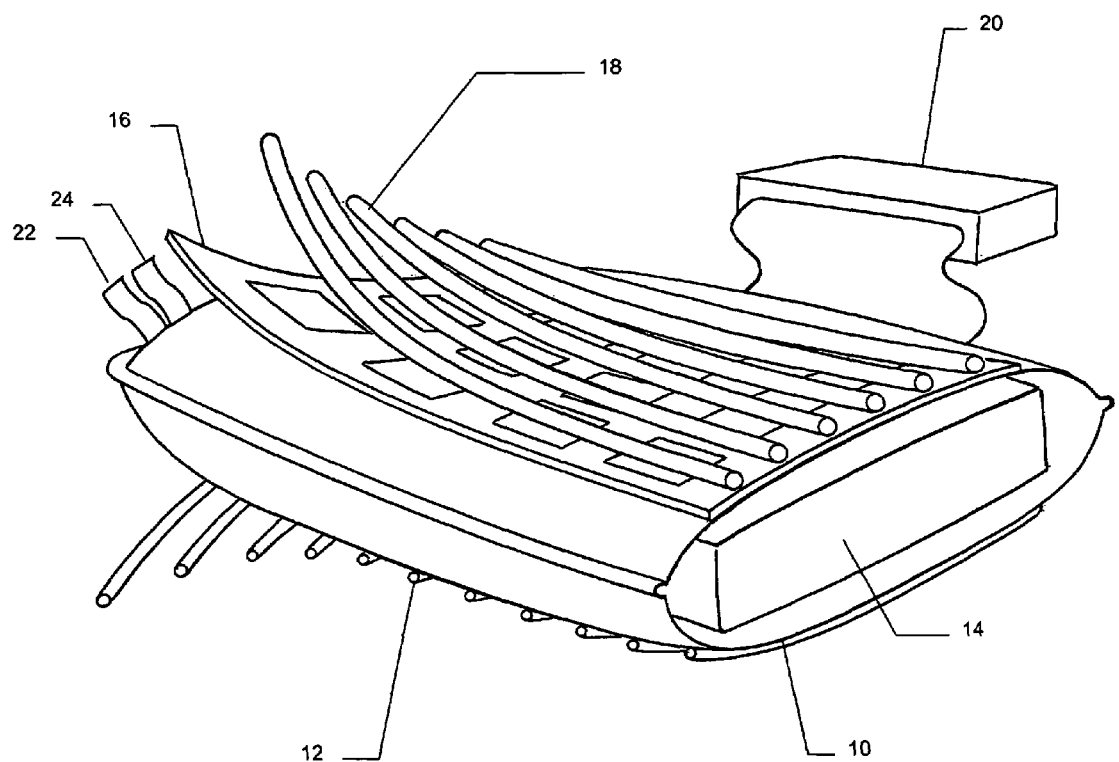
FIG. 2 is a two-point perspective view showing a cross-section of the interior components of an applicator in accordance with the invention.

Over at least a portion of the non-tissue engaging surface of the dielectric containing compartment is the heating array 16. The heating array typically comprises an antenna array for delivering electromagnetic radiation. The antenna array is preferably comprised of at least one flexible printed circuit board (PCB) that can be connected to one or more radio frequency or microwave power sources 36 (see FIG. 5) via one or more RF connectors, such as the multiport connector 20, for example, shown in FIGS. 2, 3 and 4. Alternatively, the heating array can be comprised of an array of ultrasound transducers mounted within or behind the dielectric containing compartment 10. As described below in further detail, a second thermally and electrically insulating dielectric spacer with lateral dimensions similar to the heating array can be located on the outer surface of the array. Catheters, channels or other conduits 18 are attached to the assembly and can accommodate moving or stationary radiation sources from a radiation delivery system 40 via connectors 42 (see FIG. 5). Additional catheters, channels or other conduits 12 may be located on the tissue contacting surface of the dielectric containing compartment to accommodate moving or stationary temperature monitoring sensors.

This applicator can be used to apply radiation either simultaneously or in close association with heat to a superficial tissue volume located directly under the applicator. Preferably, open lumen catheters (or channels) of appropriate diameter (e.g., 1-2 mm) cross the applicator surface parallel to each other and with a regular spacing (e.g., 5-50 mm) to accommodate moving or stationary radiation sources and moving or stationary temperature sensor probes (i.e., thermocouples, thermistors, or fiberoptic probes). These catheters or channels may be on the front, back, or both surfaces of the bolus 10 such that they directly touch the tissue (e.g., for thermal mapping) or are separated from the tissue by a fixed distance<3 cm but preferably 3-15 mm (e.g., for radiation sources). Alternatively, the open lumen channels may be formed inside the dielectric containing compartment 10 which itself is formed of either solid or liquid dielectric or both. In addition, one or more stationary temperature sensors could be affixed to the tissue-engaging surface of the dielectric containing compartment 10, or could be placed on the tissue to be treated separately from the combination applicator of this invention. Such temperature sensors could be used to provide automatic feedback control of, for example, the microwave power to individual antennas of the heating array 16.

Preferred embodiments of the invention comprise a dielectric "bolus" compartment 10, forming a layer that is typically 3-15 mm thick, filled with a liquid dielectric exhibiting very low loss to microwave radiation (e.g., distilled water, silicone oil, etc.), with a provision for maintaining constant thickness of the dielectric layer by using a solid, compressible but resilient and porous dielectric spacer 14 inside the liquid bolus chamber. The spacer is preferably formed of an open cell foam material, such as a polyurethane foam, which helps maintain a constant thickness while still allowing good circulation of the liquid dielectric through the compartment 10. The liquid dielectric is preferably temperature controlled, deionized and degassed water.

The back or non-tissue-engaging surface of the bolus 10 will have an array of heating devices 16, preferably radio frequency or microwave heating antennas or ultrasound transducer crystals. A typical embodiment would be a flexible printed circuit board conformal array of microstrip microwave antennas as described, e.g., in U.S. Pat. No. 6,330,479, entitled "Microwave Garment for Heating and/or Monitoring Tissue," and incorporated herein by reference. The front or back surface of the applicator may optionally contain a second array of microwave antennas (preferably the same number and spacing as the heating antennas) for use as radiometric receive antennas for non-invasive measurement of subsurface temperatures under the applicator via microwave radiometry.

The relatively thin, flexible applicator of the invention is especially suited for placement on the skin surface over an area of superficial disease (e.g. chestwall recurrence of breast carcinoma, melanoma, psoriasis, etc.) and may be held in place over the target region with elastic fasteners or stretchable overgarment 34. Alternatively, a low profile, malleable, form fitting, and form-holding applicator may have advantages for treating some tissue sites of complex geometry (e.g. elbow, knee, axilla, neck, forehead). Radiation therapy is delivered to the disease either by afterloading one or more of the catheters/channels 18 with brachytherapy seed arrays (e.g. IR-192, I-125, etc) or via computer controlled movement of high activity high dose rate ("HDR") sources in and out of the catheters/channels with pre-planned dwell times at numerous positions along each conduit to deliver a uniform, precisely controlled radiation dose distribution to the superficial disease as prescribed. The brachytherapy catheters may be connected to, as an example, a microSelectron HDR afterloading system (available from Nucletron, Veenendaal, The Netherlands) via a set of connecting tubes supplied with that system (not shown).

Hyperthermia therapy (e.g. 41-45° C. for 15-120 min) may advantageously be delivered by applying microwave power (typically 430-2450 MHz, but potentially 25 kHz-5 GHz) to a conformal array of microwave antennas on the 3-15 mm thick bolus back surface, either simultaneously or very close in time to the radiation dose for synergistic interaction of heat and radiation effects.

Figure 5:
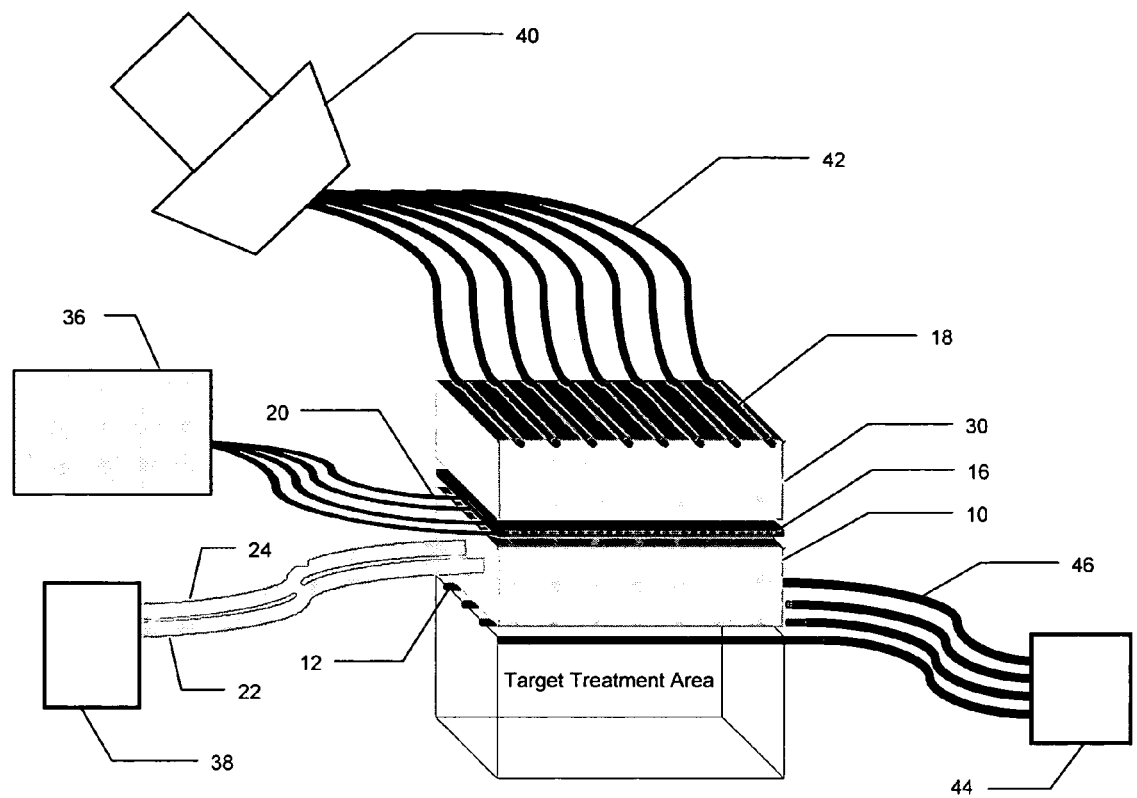
FIG. 5 is a schematic view of an embodiment of the invention.

Generally, if the bolus 10 contains a fluid dielectric, it is most preferred that the fluid is circulated through the bolus and an external heat exchanger 38, as shown in FIG. 5, maintains a uniform controlled temperature of the tissue surface in contact with the bolus. For this purpose, the flexible, dielectric containing compartment 10 may be provided with inlet and outlet ports that are connected, via hoses 22 and 24 or the like, to the external heat exchanger 38.

The radiation dose distribution may preferably be made uniform by computer-calculated dosimetry of the radiation source locations and dwell times. The dwell time distribution can be determined for planar and contoured geometries using available optimization schemes for conformal implant arrays. The temperature distribution may be made uniform by power adjustments to the multiple antenna array in response to measured temperatures of the target tissue volume.

Figure 3:
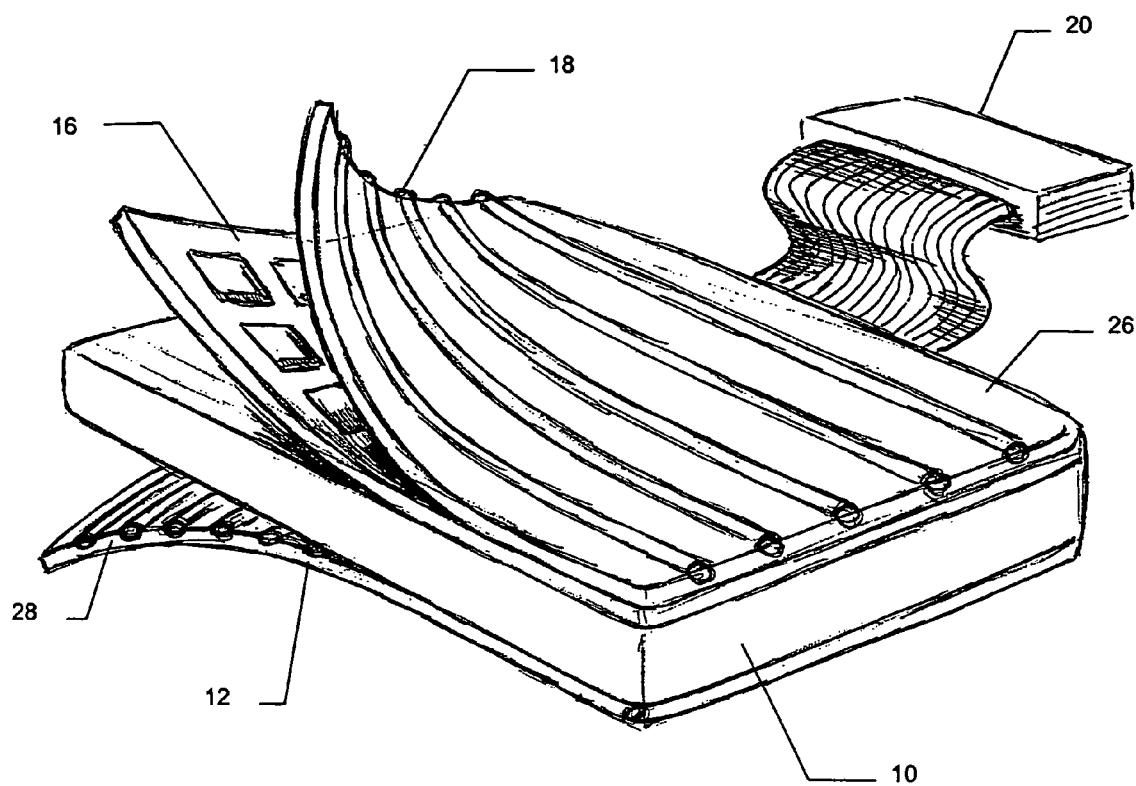
FIG. 3 is a two-point perspective view of an alternative embodiment of an applicator in accordance with the invention.

In an alternate embodiment shown in FIG. 3, the catheters, channels or other conduits 18 for accommodating the moving or stationary radiation sources can be incorporated into a sheet 26 of material secured over top of the heating array 16. In a similar fashion, the other catheters, channels or conduits 12 located on the tissue contacting surface of the dielectric containing compartment 10 for accommodating moving or stationary temperature monitoring sensors can be incorporated into a separate sheet of material 28 adjacent to the tissue contacting surface of the dielectric containing compartment. The conduits 12 can be connected to a temperature monitoring device 44 via connectors 46.

Figure 4:
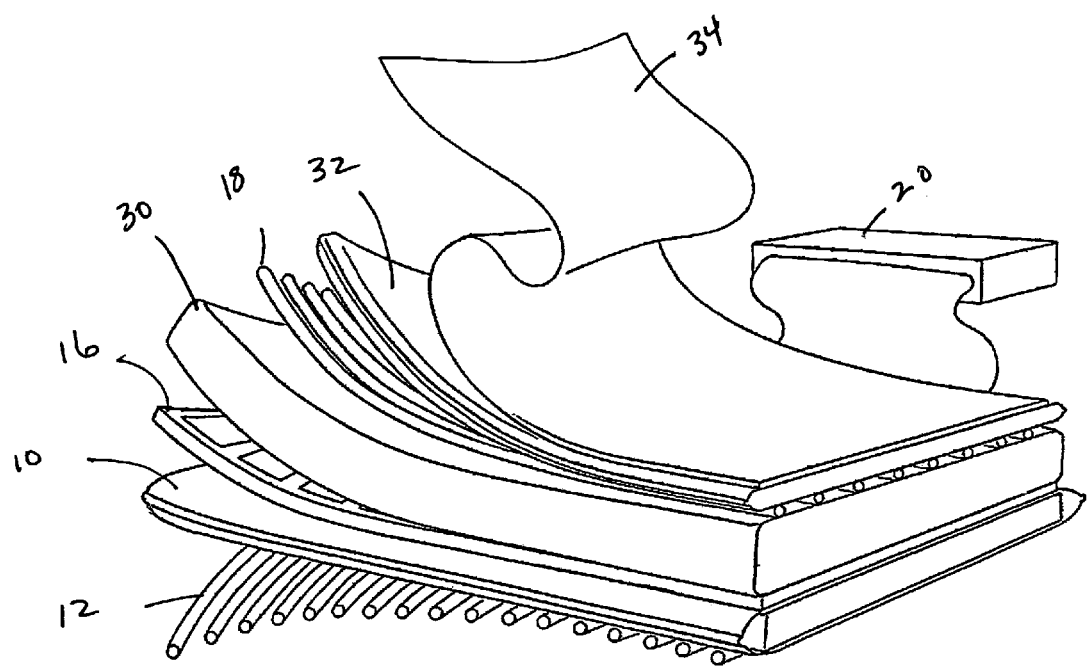
FIG. 4 is a two-point perspective view showing a cross-section of the interior of an alternative embodiment of an applicator in accordance with the invention.

In the embodiment shown in FIG. 4, the combination applicator is further provided with a second dielectric spacer layer 30 between the heating array 16 and the brachytherapy conduits 18. The dielectric spacer 30 provides additional separation between the tissue to be treated and the brachytherapy conduits 18. Thus, optimum radiation source to tissue distance may be readily obtained by adding the appropriate thickness dielectric spacer 30 over the heating array 16. In addition, the second spacer 30 may preferably be formed of a thermally insulating material to help protect the brachytherapy conduits or catheters from heat generated by the heating array.

As further illustrated in the embodiment of FIG. 4, the applicator may also be provided with an inflatable bladder 32 over top of the brachytherapy conduits/catheters 18 to improve coupling of the combination applicator to the potentially complex, twisting anatomic contours of the tissue to be treated. The inflatable bladder 32 and an outer elastic layer 34 surrounding the applicator can be used to apply gentle inward pressure over the heating array 16 and coupling bolus 10 to ensure conformity to convex as well as concave contours of the tissue surface.

Yet another alternative configuration may use a stationary array of radioactive brachytherapy sources (e.g. iridium, iodine) which are afterloaded into all catheters 18 on the non-tissue contacting surface of the coupling bolus which may provide for longer term continuous low dose rate (LDR) radiotherapy simultaneously with long duration moderate temperature hyperthermia therapy.

In accordance with the provisions of the patent statutes, the invention has been described in what is considered to represent its preferred embodiments. However, it should be noted that the invention can be practiced otherwise than as specifically illustrated and described without departing from its spirit or scope.

What is claimed:

1. A flexible, conformal heat and radiation delivering applicator comprising:
    a flexible, dielectric containing compartment having a tissue-engaging surface and an opposite, non-tissue-engaging surface;
    a dielectric fluid circulated through the dielectric containing compartment;
    a heating array supported over the non-tissue-engaging surface of the compartment; and
    a plurality of brachytherapy conduits supported over the dielectric containing compartment, the brachytherapy conduits being in communication with at least one brachytherapy radiation source.

2. The applicator of claim 1, wherein the heating array comprises a plurality of microwave antennas for delivering electromagnetic radiation to tissue.

3. The applicator of claim 1, wherein the heating array comprises a plurality of radiofrequency electrodes for delivering electromagnetic radiation to tissue.

4. The applicator of claim 1, wherein the heating array comprises at least one flexible printed circuit board.

5. The applicator of claim 4, wherein the flexible printed circuit board is comprised of an array of radiating structures driven with at least one power source at a frequency within the range of 25 kHz-5 GHz and power level in the range of 0-1000 Watts.

6. The applicator of claim 1, wherein the heating array comprises a plurality of ultrasound transducer crystals for delivering ultrasound energy to tissue.

7. The applicator of claim 1, wherein the flexible, dielectric containing compartment has a substantially constant thickness less than or equal to 5 cm and is adapted to transmit heat and radiation uniformly into tissue overlying contoured anatomy, and to control the temperature of tissue surface.

8. The applicator of claim 1, wherein the conduits are for thermal probe mapping and brachytherapy delivery and comprise catheters or open lumen channels.

9. The applicator of claim 1, further comprising at least one non-invasive temperature monitor supported adjacent to the tissue-engaging surface of the compartment.

10. The applicator of claim 9, wherein the at least one non-invasive temperature monitor is placed within at least one catheter or conduit positioned adjacent the tissue-engaging surface.

11. The applicator of claim 9, wherein the temperature monitor comprises a radiometric imaging device located on a flexible printed circuit board.

12. The combination applicator of claim 1, further comprising a solid, resilient and porous dielectric spacer housed inside the dielectric containing compartment.

13. The applicator of claim 1, wherein the dielectric fluid is temperature controlled.

14. The applicator of claim 13, wherein the dielectric fluid is comprised of deionized and/or degassed water.

15. The applicator of claim 1, further comprising a dielectric spacer positioned between the heating array and the plurality of brachytherapy conduits.

16. The applicator of claim 1, further comprising an inflatable bladder positioned over the plurality of brachytherapy conduits.

17. The applicator of claim 1, further comprising an outer elastic layer positioned over the plurality of brachytherapy conduits.

18. The applicator of claim 16, further comprising an outer elastic layer positioned over the inflatable bladder.

19. The applicator of claim 1 utilized to treat biologic tissue with heat delivered in combination with brachytherapy radiation.

20. The applicator of claim 1 utilized to treat biologic tissue with heat delivered in combination with brachytherapy radiation and chemotherapy.

21. The applicator of claim 1 utilized to treat biologic tissue with mild hyperthermia at temperatures within the range of 40-45° C. in combination with radiation.

22. The applicator of claim 1 utilized to treat biologic tissue with ablative temperatures within the range of 45-100° C. in combination with radiation.

23. The applicator of claim 1, wherein the plurality of brachytherapy conduits is supported over the heating array such that the heating array is positioned between the brachytherapy conduits and the dielectric containing compartment.

24. A flexible, conformal heat and radiation delivering applicator comprising:
    a flexible, dielectric containing compartment having a tissue-engaging surface and an opposite, non-tissue-engaging surface;
    a dielectric fluid circulated through the dielectric containing compartment;
    a heating array supported over the non-tissue-engaging surface of the compartment;
    a dielectric spacer supported over the heating array; and
    a plurality of brachytherapy conduits supported over the dielectric spacer, the brachytherapy conduits being adapted for communication with at least one brachytherapy radiation source.

* * * * *